United States Patent [19]  [11]  4,253,469
Aslan  [45]  Mar. 3, 1981

[54] IMPLANTABLE TEMPERATURE PROBE
[75] Inventor: Edward E. Aslan, Plainview, N.Y.
[73] Assignee: The Narda Microwave Corporation, Plainview, N.Y.
[21] Appl. No.: 31,841
[22] Filed: Apr. 20, 1979

Related U.S. Application Data

[62] Division of Ser. No. 802,115, Mar. 31, 1977, Pat. No. 4,182,313.

[51] Int. Cl.³ ............................................. A61B 0/00
[52] U.S. Cl. ............................... 128/736; 73/359 R
[58] Field of Search ............... 128/633, 736, 422, 804; 73/341, 359 R

[56] References Cited
U.S. PATENT DOCUMENTS 2,816,997  12/1957  Conrad .................................. 128/736
4,108,163  8/1978  Fleckenstein et al. ............... 128/736
4,110,124  8/1978  Robertson .......................... 73/359 R

OTHER PUBLICATIONS

Larsen et al., "IEEE Transactions on Microwave Theory + Techniques", vol. 22, No. 4, Apr., 1974, pp. 438-444.

Primary Examiner—William E. Kamm
Attorney, Agent, or Firm—James A. Eisenman; Robert R. Strack

[57] ABSTRACT

A temperature probe that does not perturb incident electromagnetic fields which includes a high resistance thermocouple mounted within a rigid needle structure. Special leads connect the thermocouple to appropriate metering means to register the temperature sensed by the thermocouple.

6 Claims, 9 Drawing Figures

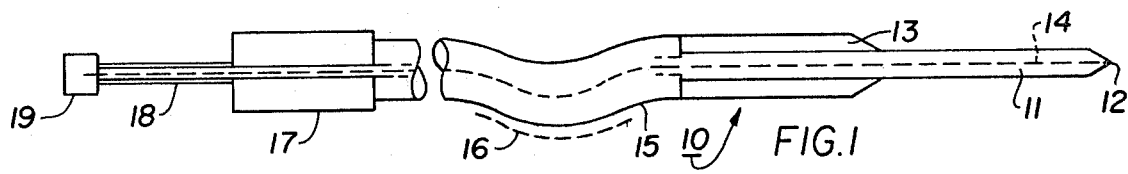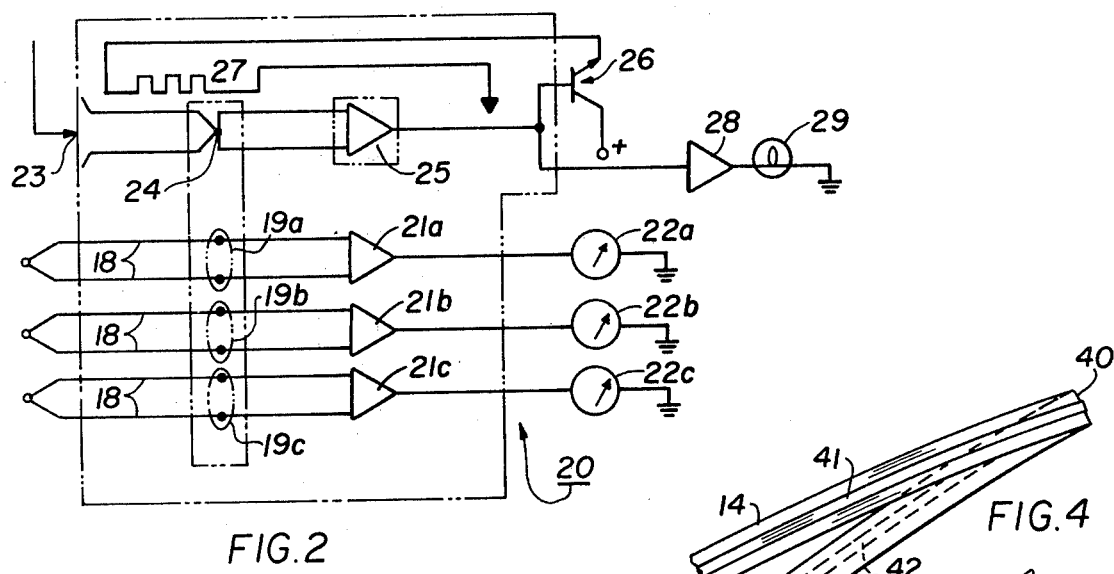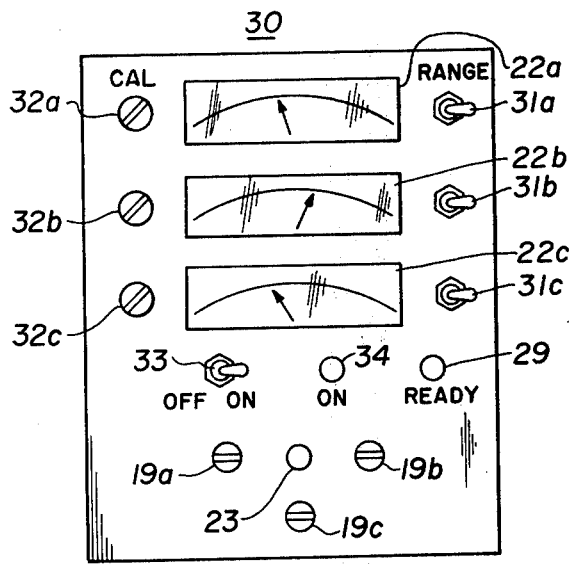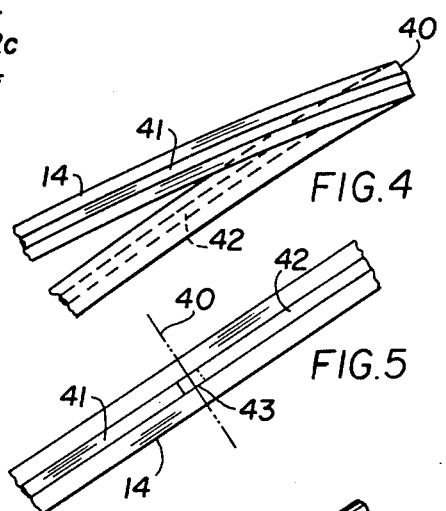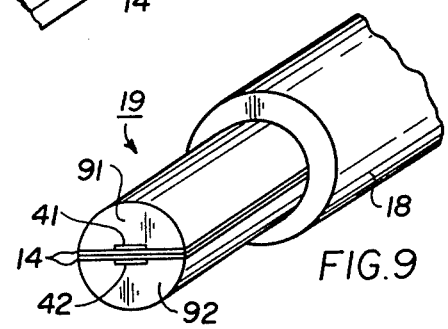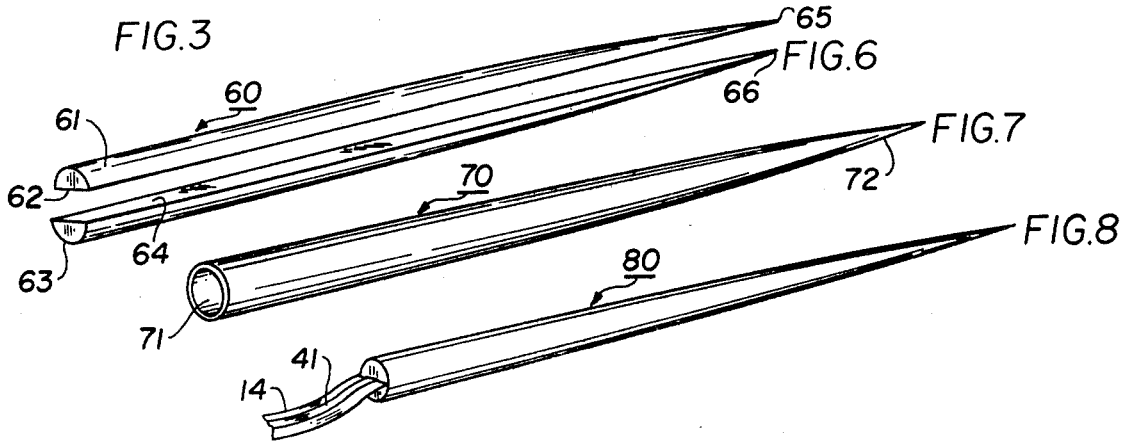

IMPLANTABLE TEMPERATURE PROBE

CROSS-REFERENCE TO RELATED APPLICATION

This is a division of co-pending application Ser. No. 802,115, filed May 31, 1977 now U.S. Pat. No. 4,182,313.

BACKGROUND OF THE INVENTION

This invention relates to temperature sensing devices and more particularly to temperature sensing devices that can be implanted within the body of humans or other animals.

Research has disclosed that tissue and tumors in animals may be destroyed by a selective increase in temperature. Relatively small elevations of temperature are adequate to effect destruction. When this technique is used to destroy tumors, great care must be taken to avoid injury to the surrounding tissue. Accordingly, it is important to precisely monitor the temperature of the tumor and the surrounding tissue.

While the desired heating may be accomplished in a variety of ways, the present application is principally concerned with operations wherein an electromagnetic field is used. In the presence of such a field, many temperature sensing devices either become inoperative or perturb the field and adversely affect the procedure. Any conductive material, line or element, placed within an electromagnetic field will have a radio frequency current induced within it. Such a current in turn causes a new electromagnetic field to be established and such a new field alters the original incident field. It has been found that by utilizing extremely high resistances in the temperature monitoring unit, negligible current will flow and there will therefore be no perceptible perturbation of the incident field. Furthermore, by utilizing high resistance within the monitoring unit, the negligible currents that are induced will provide extremely low power dissipation and hence there is negligible localized heating originated by the unit itself.

DESCRIPTION OF THE PRIOR ART

A variety of temperature probes have been recently proposed. One such unit employs a liquid crystal located at the end of a fiber optics bundle and measures temperatures within a limited range. Since this probe has no metallic components it has little effect upon electromagnetic radiation. Another unit uses a thermistor and plastic high-resistance leads. The thermistor resistance is sensed by injecting a constant current through a first pair of leads while measuring the voltage developed across the thermistor with a high impedance amplifier connected to a second pair of leads. Still another unit consists of a microwave integrated circuit electrode having a transducer that is glass encapsulated and a hyper-thin transmission line for r-f decoupling.

SUMMARY OF THE INVENTION

According to the present invention there is provided a thermo electric device for in vivo temperature measurements. The device does not perturb or distort incident electromagnetic fields that may be illuminating the tissue in which it resides.

An object of the invention is to provide an improved temperature sensing device.

Another object of the invention is to provide an improved temperature sensing device appropriate for implanting within animal tissue.

Yet another object of the invention is to provide an improved temperature sensing device that is substantially nonresponsive to electromagnetic fields.

In accordance with one embodiment of the invention an implantable temperature probe comprises a thin film thermocouple of high resistivity on a thin dielectric substrate mounted upon or in a rigid dielectric rod or needle. The component metals of the termocouple are supported beyond the distal end of the rod by a flexible continuation of the substrate and thereafter connected at a reference junction that is maintained at a constant temperature by a proportional oven.

A complete understanding of the invention, an appreciation of its features, and the manner in which the above objects are attained, will be available from the following description which is made in conjunction with the drawings.

BRIEF DESCRIPTION OF THE DRAWINGS

FIG. 1 is a schematic illustration of a temperature probe embodying the invention;

FIG. 2 is a schematic illustration of an oven adapted to receive the inputs from three temperature probes and provide an amplified output for the driving of calibrated meters;

FIG. 3 is an illustration of a typical metering instrument having dials for displaying the temperature sensed by three probes in accordance with the invention;

FIGS. 4 and 5 show mounting of a thermocouple for use as the temperature sensitive element in the temperature probe of the invention;

FIG. 6 illustrates one embodiment of the invention wherein insulated semi-circular rods are employed to form the needle portion of the probe;

FIG. 7 illustrates a second embodiment of the invention wherein a hollow conical rod is utilized as the needle portion of the invention;

FIG. 8 is a schematic illustration of the needle portion of the invention prior to assembly as a complete unit; and FIG. 9 is a detail view showing the connector at end of a temperature probe.

DESCRIPTION OF PREFERRED EMBODIMENTS

As shown in FIG. 1, the front end of an implantable temperature probe 10 comprises a needle 11 suitable for insertion within the tissue and serving as the carrier for a high resistivity thin film thermocouple located near tip 12. The distal end of needle 11 is protected by a rigid insulating plastic material 13 which in turn is connected to a flexible plastic conduit 15 which may be coated with a resistive shield 16 in order to eliminate build-up of static charges. This flexible portion 15 must be of sufficient length for convenient utilization of the probe while its remote end is connected to a metering device.

As FIG. 1 also shows, the lead wires 14 which extend backward from tip 12, pass through a capacitance shield 17 which is kept in close proximity to a proportional oven (FIG. 2). The lead wires then proceed from the capacitance shield 17 to a connector structure 19 that is illustrated in greater detail in FIG. 9.

FIG. 2 illustrates an oven 20 capable of handling the inputs from three probes of the type shown in FIG. 1. Each input finds connector 19 coupled into the oven via female counterpart 19a, 19b, or 19c. The inputs are amplified by amplifiers 21a, 21b, or 21c and supply the driving input to meters 22a, 22b, or 22c respectively. The proportional oven 20 establishes the reference junction temperature. This is accomplished by using a thermistor 24 driving an operational amplifier 25. The desired temperature is effected by a conventional calibrated temperature sink 23. Amplifier 25 via feedback transistor 26 drives a heater 27 in order to maintain the temperature within close limits. In a typical operation, the connector end 19 is the reference junction and it is maintained at a constant temperature level of approximately 41 degrees Centigrade.

FIG. 3 shows an instrument panel 30 arranged to service three temperature probes of the type contemplated by this invention. The connectors 19 of each probe would be coupled to the instrument panel and thence to the oven of FIG. 2, via the female portion of connectors 19a, 19b, and 19c. Adjustment of the calibrated temperature sink 23 may be done via conventional adjustment means by control of operational amplifier 25. The panel includes an on-off switch 33, an "on" signal light 34, and a ready light 29 that is energized when the oven has reached the desired temperature level, via amplifier 28 (shown in FIG. 2). Each of the three meters 22a, 22b, and 22c, is serviced by a calibrating element 32a, 32b, 32c and a typical scale adjustment switch 31a, 31b, 31c for selecting desired ranges for each meter (for example, the switch may select a full range of 1 degree Centigrade or 5 degrees Centigrade, depending upon the desires of the operator). The particular panel layout is not germane to the invention and simply illustrates the manner in which conventional controls may be incorporated to provide desired results when using this invention.

FIG. 4 illustrates the basic temperature sensitive thermocouple portion of the invention. A flexible insulating material 14, such as Kapton, is provided in thin film form as the substrate for the metallic elements 41, 42 that form the thermocouple. Typically, one might select antimony for portion 41 and bismuth for portion 42.

As seen in FIG. 5, the two metallic films 41, 42 overlap at a central point 40 to form the hot junction 43. This hot junction is available near the tip of the final assembly because the substrate 14 is folded over as illustrated in FIG. 4. The structure is designed so that the front end of the thermocouple resistivity is high, in the order of 50 ohms per square with line widths of approximately 0.003 inches. In a particular embodiment, the resistance of the first foot was a nominal 2000,000 ohms.

Since the bi-metallic material on its substrate, is insufficiently rigid, it must be mounted within a needle or otherwise rigidized, so that it will be possible to implant the hot junction in the region desired. FIGS. 6 and 7 show several needle structures. The configuration of FIG. 6 illustrates two separate semi-circular conical portions having flat faces 61, 64 facing each other. FIG. 7 illustrates an enclosed conical element 70 having an aperture 71 adapted to accept the folded over thermocouple unit of FIG. 4.

When using either of the structures suggested in FIGS. 6 and 7, the flexible folded thermocouple carrier is bonded within the needle tip with the hot junction 43 as close to the point as possible. When the separate halves of FIG. 6 are used, after bonding, the projecting portions of the thermocouple strip may be filed or ground down in order to provide a uniform surface throughout the length of the needle yielding the structure illustrated in FIG. 8. It has been found that a sapphire rod having a diameter in the range of 0.01 inches, serves as a good needle vehicle. Suitable flexibility and insulating characteristics for the substrate 14, are available from a Kapton or plastic substrate.

In accordance with the invention, the flexible substrate 14 with extending resistive leads 41, 42 is maintained intact throughout the length of the probe shown in FIG. 1. The distal end of the needle portion may advantageously have a rigid shield 13 or tube of Teflon material bonded thereto. Following this portion, a more flexible tubing 15 advantageously coated with a resistive static charge shield 16 runs the entire length of the probe, which may be four feet or so. At the remote end of the probe an aluminum capacitance shield 17 or the like is provided in close proximity to the connector 19.

The connector 19 serves the basic function of providing an input to the oven shown in FIG. 2. This must be accomplished while maintaining the high resistivity of the probe itself, and with minimum modification of the resistivity of each of the component metals 41, 42. A convenient way of achieving this is to provide two semi-circular portions for sandwiching the flexible metal bearing substrate 14 therebetween. In FIG. 9, each portion 91, 92 is fabricated of the same material as the metal against which it butts. Thus, if metal 41 is antimony, antimony is used to form portion 91. Similarly, if metal 42 is bismuth, portion 92 will also be manufactured of bismuth.

In addition to using the flexible substrate 14 as the carrying vehicle at the tip of needle 11, one may elect to vacuum deposit the metals forming the thermocouple onto the flat surfaces 62, 64 of split sapphire rods, or the like, as shown in FIG. 6. Where this manufacturing technique is used, an insulating sheet would be sandwiched between the halves, before bonding.

A particular implantable temperature probe has been shown and described. Those skilled in the art will appreciate that modifications may be made in dimensions and materials without departing from the spirit and teachings of this disclosure. All such modifications coming within the skill of the art are intended to be embraced by the following claims.

What is claimed is:

1. An implantable bi-metallic temperature sensing unit comprising: a rigid needle having a hollow substantially conical portion designed to penetrate animal tissue; an elongated substrate; a high resistance thermocouple including two overlapped metallic films bonded substantially along the longitudinal axis on one face of said elongated substrate, said substrate being folded back upon itself where said films overlap and being inserted into said conical portion to position the overlapping area in close proximity to the tip thereof; a meter means and flexible lead means extending from the distal end of said needle for connecting signals from said thermocouple to said meter means, said lead means including a resistive static charge shield and resistive material having characteristics similar to that of the metals in said bi-metallic thermocouple, and said needle including materials having resistance to limit the energy coupled from incident radio frequency fields.

2. An implantable sensing unit as defined in claim 1, wherein said flexible lead means terminates in a rigid connector having contacts formed of the same material as the bi-metallic thermocouple.

3. An implantable bi-metallic temperature sensing unit comprising: a rigid needle including materials having resistance to limit the energy coupled from incident radio frequency fields and having a hollow substantially conical portion designed to penetrate animal tissue; an elongated substrate; a high resistance thermocouple including two overlapped metallic films bonded substantially along the longitudinal axis on one face of said elongated substrate, said substrate being folded back upon itself where said films overlap and being inserted into the conical portion of said needle to position the overlapping area in close proximity to the tip thereof; a meter means; flexible lead means extending from the distal end of said needle for connecting signals from said thermocouple to said meter means, said lead means including resistive material having characteristics similar to that of the metals in said bi-metallic thermocouple; and a proportional oven, amplifier means within said oven, means connecting said flexible leads to said amplifier means, and means coupling the output of said amplifier means to said meter means.

4. An implantable sensing unit as defined in claim 3, including means within said proportional oven to establish the temperature of the reference junction whereat said flexible leads are connected to said amplifier means.

5. An implantable bi-metallic temperature sensing unit as defined in claim 3, wherein said flexible lead means includes a resistive static charge shield.

6. An implantable bi-metallic temperature sensing unit as defined in claim 5, wherein said flexible lead means terminates in a rigid connector having contacts formed of the same material as the bi-metallic thermocouple.

* * * * *